United States Patent
Pospisilik et al.

(10) Patent No.: US 6,770,761 B2
(45) Date of Patent: Aug. 3, 2004

(54) PROCESS FOR PREPARATION OF 2-AMINO-6 (ALKYL) AMINO-4,5,6,7-TETRAHYDROBENZOTHIAZOLES

(75) Inventors: Karel Pospisilik, Brno (CZ); Hans Jan Hoorn, Nijmegen (NL); Theodorus Hendricus Antonius Peters, Arnhem (NL); Jacobus Maria Lemmens, Mook (NL)

(73) Assignee: Synthon BV, Nijmegen (NL)

( * ) Notice: Subject to any disclaimer, the term of this patent is extended or adjusted under 35 U.S.C. 154(b) by 8 days.

(21) Appl. No.: 10/380,758

(22) PCT Filed: Sep. 14, 2001

(86) PCT No.: PCT/NL01/00680

§ 371 (c)(1),
(2), (4) Date: Aug. 7, 2003

(87) PCT Pub. No.: WO02/22590

PCT Pub. Date: Mar. 21, 2002

(65) Prior Publication Data

US 2004/0029936 A1 Feb. 12, 2004

(30) Foreign Application Priority Data

Sep. 18, 2000 (ES) ............................................. 200002262

(51) Int. Cl.$^7$ ............................................. C07D 277/82

(52) U.S. Cl. ........................................................ 548/161
(58) Field of Search ........................................... 548/161

(56) References Cited

FOREIGN PATENT DOCUMENTS

| EP | 0 186 087 A | 7/1986 |
|----|-------------|--------|
| EP | 0 251 077 A | 1/1988 |

OTHER PUBLICATIONS

Kozikowski A P, et al., "Synthesis of the thiazolone analogue of the acetylcholinesterase inhibitor, huperzine A," Helvetica Chimica Acta, vol. 77, No. 5., 1994, pp 1256–1266.
Schneider C S, et al., "Dopamine autoreceptor agonists: Resolution and . . ." J. Medicinal Chem., vol. 30, No. 3, 1987, pp 494 498.

*Primary Examiner*—Taofiq Solola
(74) *Attorney, Agent, or Firm*—Mark R. Buscher

(57) ABSTRACT

A new process to obtain pramipexole and related products is described. The process involves the reaction of new compounds of formula (6), wherein R is hydrogen or acyl group, $R_3$ and $R_4$ are either the same and each of them represents an alkoxy group of 1–4 carbons or they together form a $C_2$–$C_5$ alkylenedioxy group or an oxo-group, with an alkylamine in the presence of a reducing agent or a hydrogen gas with hydrogenation catalyst. A process to obtain new compounds of formula (6) is also described.

23 Claims, No Drawings

US 6,770,761 B2

1

PROCESS FOR PREPARATION OF 2-AMINO-6 (ALKYL) AMINO-4,5,6,7-TETRAHYDROBENZOTHIAZOLES

This application is a 371 of PCT/NL01/00680 filed Sep. 4, 2001.

The present invention relates to a novel process for preparing 2-amino-6-alkylamino-4,5,6,7-tetrahydrobenzothiazoles and to certain intermediates useful therein.

BACKGROUND AND PRIOR ART

The 2-(acyl)amino-6-(substituted)amino-4,5,6,7-tetrahydrobenzothiazoles having the general formula (1):

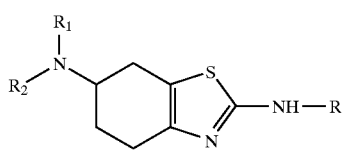

(1)

wherein R is hydrogen or acyl group, $R_1$ is hydrogen, alkyl or aralkyl group and $R_2$ is hydrogen, are useful pharmaceutical agents. Some of these compounds are known to have dopamine D-2 agonist activity. The compounds of formula (1) include S(−)-2-amino-6-propylamino-4,5,6,7-tetrahydrobenzothiazole (pramipexole) of the formula (2)

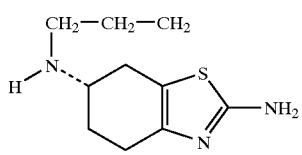

(2)

which is a commercial product used for treatment of Parkinson's disease and schizophrenia and is marketed, in a form of a dihydrochloride, under several brand names e.g. Mirapexin[TM].

The compounds of formula (1) are described in EP 186087.

Several methods for preparing compounds of the above formula (1) are suggested in EP 186087 and EP 207696. A common core of these methods is a process comprising ring halogenation preferably bromination) of a substituted aminoketone (3) and the condensation of the so obtained alpha-halogenaminoketone (4) with thiourea or N-acylthiourea to form a 2-aminotetrahydrobenzothiazole ring, as shown in the following scheme:

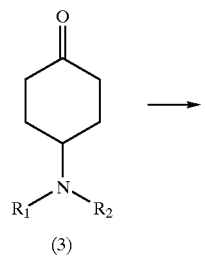

(3)

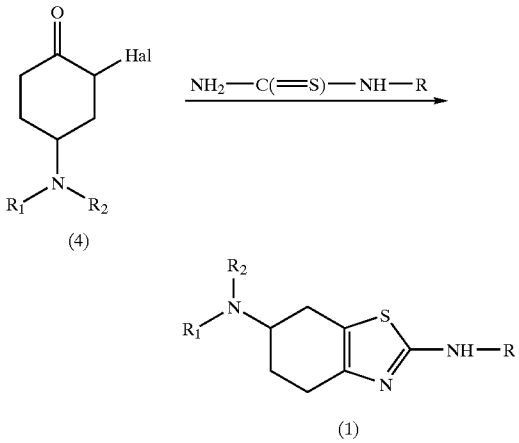

(4)

(1)

Dependent on the nature of substituents $R_1$, $R_2$ in (3) and (4) and on the desired structure of the product (1), the corresponding amino substituents which are desired to be in position 6 of compounds (1) may or have to be accordingly modified before and after this two-step condensation.

A compound of formula (1), wherein both $R_1$ and $R_2$ are hydrogen, is prepared from a compound (3) wherein either $R_1$ is an amino-protective group such as an acyl or alkoxycarbonyl group and $R_2$ is hydrogen or $R_1$–$R_2$ together form an imino-protective group such as phthalimidogroup. After halogenation and condensation with thiourea, the protective group is removed in a separate step.

A compound of formula (1), wherein $R_1$ is acyl and $R_2$ is hydrogen, is prepared from a compound (3) wherein $R_1$ is acyl and $R_2$ is hydrogen.

A compound of formula (1), wherein $R_1$ is alkyl or aralkyl and $R_2$ is hydrogen, is either prepared from a compound (3) wherein $R_1$ is alkyl or aralkyl and $R_2$ is hydrogen or a protective group (with subsequent deprotection in that later case), or it can be prepared by alkylation/aralkylation of the compound (1) wherein both $R_1$ and $R_2$ is hydrogen or, finally, it can be prepared by metal hydride or borane reduction of the acyl group in a compound of formula (1) wherein $R_1$ is acyl or arylacyl and $R_2$ is hydrogen.

In all the above cases, the acyl substituent R should be furthermore hydrolysed to hydrogen, whenever necessary.

If desired, the produced compounds of formula (1) may be converted into salts with inorganic and organic acids, particularly with acids which are pharmaceutically acceptable.

Thus, in total, the overall synthetic process represents a sequence of at least four synthetic steps. In practice, a primary aminogroup or a secondary alkylaminogroup present in the compounds of formula (1) cannot be introduced and maintained during oxidation, bromination and cyclization step without introduction a protective group, due to its reactivity. The protective group must be removed afterwards.

In the case of pramipexole and similar compounds, the following synthetic sequence from the cited prior art is suggested to be most useful.

The last step of the overall synthesis comprises reductive alkylation of 2,6-diamino-4,5,6,7-tetrahydrobenzothiazole (compound (1), $R_1$=$R_2$=H), e.g. by propionaldehyde/sodium borohydride; the starting diamino-compound has been prepared by a sequence starting from 4-aminocyclohexanol which has been acetylated or phthalidated and subsequently oxidised to yield acetamido- or 4-phthalirnidocyclohexanone which has been monobrominated and subsequently reacted with thiourea to give 6-acetamido (or 6-phthalimido)-2-amino-4,5,6,7-tetrahydrobenzothiazole (compound (1), $R_1$=H, $R_2$=CO—$CH_3$ and/or $R_1$, $R_2$=phtalimido); finally, the protective acetyl or phthalimido group has been removed.

Thus, in practice, the overall synthetic sequence, starting from commonly available material, represents six synthetic steps.

In addition, the compounds of formula (1) have an asymmetric carbon and they exist either as single enantiomers and/or in a racemic form. The pharmacological activity of compounds of formula (1) is however generally connected only or mainly with one stereoisomer thereof; for instance, pramipexole is marketed as a single S(−) isomer and the dopaminergic activity of the said isomer is twice as high as that of the R(+) isomer. The cited prior art process allows preparing only a racemate. It is anticipated that, if the product of formula (1) has a chiral atom, the produced racemic compound may be resolved into optical isomers by classical methods such as chromatography or fractional crystallisation. Generally it should thus be expected that, in industrial scale, the produced racemic compounds of formula (1) are resolved into optical isomers by adding a next production sequence comprising steps of forming a salt with an appropriate optically active acid, resolution of salts by fractional crystallisation and, if necessary, liberating the free base of the resolved product from the salt. An example of such resolution process in the case of producing optically pure pramipexole has been disclosed by Schneider and Mierau in J. Med. Chem 30, 494 (1987), using the diaminoderivative (compound (1), R=$R_1$=$R_2$=H) as a substrate and L(+) tartaric acid as a resolution agent. Following to the resolution, optically active pramipexole has been prepared by two-step propylation of the single enantiomer of the diamino-precursor comprising reaction with propionanhydride followed by reduction of the propionyl intermediate.

It is apparent that the prior art processes for preparing compounds of formula (1) suffers from severe drawbacks, as they are lengthy and economically undesirable. Thus, there exist a need for a more straightforward production process.

DESCRIPTION OF THE INVENTION

As the result of the present inventors' continuous study to establish a more economical and simple process for producing compounds of formula (1), a novel, straightforward and efficient process has been found enabling synthesis of compounds (1) in two steps from easily available 1,4-cyclohexanedione, by employing novel intermediates and a novel way of conversion of such new intermediates to compounds (1). Particularly, the process of our invention raises a potential to prepare the compound (1) enriched by a single enantiomer thereof.

According to the first aspect of the present invention, there is provided a process for preparing compounds of formula (1)

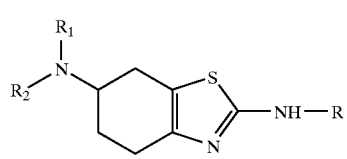

(1)

wherein R is hydrogen or acyl group, $R_1$ is hydrogen, lower alkyl or aralkyl group and $R_2$ is hydrogen, comprising a reaction of a compound of formula (6),

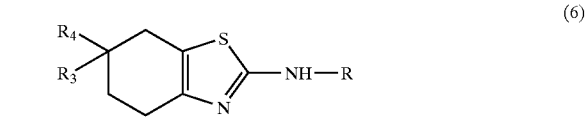

(6)

wherein R is hydrogen or acyl group, $R_3$ and $R_4$ are either the same and each of them represents an alkoxy group of 1–4 carbons or they together form a $C_2$-$C_5$ alkylenedioxy group or an oxo-group, with an amine of general formula (7)

(7)

wherein $R_1$ is as hereinbefore defined, in a presence of a reducing agent or a hydrogen gas with hydrogenation catalyst, optionally followed, if a compound (1) with R=acyl is produced, by hydrolysis of the acyl group to hydrogen, and isolation of the resulted compound of formula (1) as a free base or as an acid addition salt, incl. any hydrate or solvate thereof.

In a particular aspect, there is provided a process as defined above wherein the compound of formula (1) is produced substantially enriched by a single enantiomer, by using stereospecifically reducing agent or a chiral hydrogenation catalyst.

The compounds of formula (6) wherein $R_3$ and $R_4$ are as defined above are novel and they represent a second aspect of the present invention. As the preferred compounds, 2-amino-6-oxo-4,5,6,7-tetrahydrobenzothiazole (compound (6), R=H, $R_3$, $R_4$ is =O group), 2-amino-6,6-dimethoxy-4,5,6,7-tetrahydrobenzothiazole (compound (6), R=H, $R_3$ and $R_4$ are methoxy groups), 2-acetamido-6-oxo-4,5,6,7-tetrahydrobenzothiazole (compound (6), R=acetyl, $R_3$, $R_4$ is =O group) and 2-acetamido-6,6-dimethoxy-4,5,6,7-tetrahydrobenzothiazole (compound (6), R=acetyl, $R_3$ and $R_4$ are methoxy groups) are claimed, as well as acid addition salts thereof.

In a third aspect, the present invention provides a process for producing a compound of formula (6) wherein $R_3$ and $R_4$ are as defined above, said process comprising bromination of 1,4-cyclohexandione (5) in an alcoholic solvent to yield a compound of formula (8)

(8)

wherein $R_3$ and $R_4$ are as defined above, followed by reaction with thiourea or N-acylthiourea. In a preferred aspect, the reaction is performed without isolation of intermediate product of the general formula (8). If desired, the acyl group R may be subsequently hydrolysed to hydrogen.

The overall process of the present invention is illustrated by the following reaction scheme:

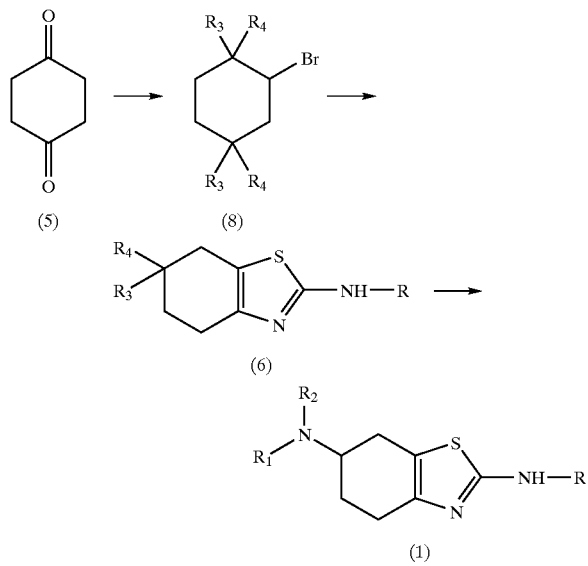

As shown by the above reaction scheme, the first step of a process of the present invention is characterised by a novel finding that 1,4-cyclohexanedione (5) can be selectively monobrominated to give an intermediate (8). Though seeming to be a simple compound, no records of successful monobromination of 1,4-cyclohexanedione (5) have been found in any prior art disclosure and the intermediate (8) has not been described and/or characterised so far.

We have found out that the monobromination of 1,4-cyclohexandione (5) cannot be achieved if attempting to brominate the substrate under "classical" conditions, e.g. by using bromine in acetic acid or in a halogenated hydrocarbon (e.g. in chloroform) and at slightly elevated temperatures, which conditions could be regarded by a skilled chemist as quite suitable for the reaction as the substrate is well soluble in these solvents. Indeed, bromine apparently reacts with the substrate, but the reaction product is different: immediate elimination of hydrogen bromide and formation of hydroquinone system follow the bromination.

After thorough experimental work resulting into our invention, we were successful in finding conditions, under which the desired compound (8) could be formed reliably. It was found that a substantial condition for successful monobromination of (5) is to perform the bromination reaction in an alcohol as a reaction medium. A relatively stable product of bromination can be obtained only under a condition if the keto-groups are masked as a ketal; the alcohol is thus also a reaction partner for such ketalization. As the alcohol, a lower alkanol of one to four carbon atoms (e.g. methanol, ethanol, n-propanol) or an alkyleneglycol of two to five carbon atoms (e.g. ethylene glycol or 2,2,-dimetylpropyleneglycol) may be employed, though other alcohols are not specifically excluded. Methanol is the most preferred alcohol for the bromination.

The proper substrate for the bromination is thus in fact a compound of formula (9)

wherein R3 and R4 either represent the same alkoxy group or they together form an alkylenedioxy group. The term "alkoxy" represents a straight or branched alkoxy group having one to four carbon atoms; the term "alkylenedioxy" represents a group wherein the alkylene moiety consists from two to five carbon atoms.

The product of the bromination of the formula (8) is indeed still a quite unstable compound. Thus, the bromination reaction should advantageously be followed by the reaction with thiourea without isolation of the compound (8); however, the step of isolation of the intermediate (8) is not specifically excluded from this invention. The second advantage of the alcoholic solvent is that it can serve as a reaction medium also for the reaction with thiourea. The primary product (6) is the ketal (i.e. $R_3$, $R_4$ are alkoxy groups or alkylenedioxy group); however, the ketal can be easily converted into a 6-oxo compound in the presence of water. Water can be either added intentionally, both after the reaction with thiourea (to the reaction mixture or to isolated ketal) and before the reaction of thiourea, or it may be present in the reaction mixture as a product of reaction from preceded steps. The deketalisation to 6-oxo compound generally requires the presence of an acid; herein, the hydrogen bromide liberated from the reaction with thiourea can serve as the acid catalyst.

It is not decisive whether the product (6) is isolated after the reaction with thiourea in a form of a ketal or as a 6-oxo compound or as a mixture of these two compounds. Both types of the substrate are equally suitable for the subsequent amination. The product (6) may be isolated as a free base or as an acid addition salt; preferred salt is a hydrobromide.

In the last (i.e. the second) production step, the isolated product (6) or the mixture of products (6) is subjected to the reductive amination with ammonia or corresponding alkylamine (7) in presence of a reducing agent to give requested compound of the formula (1). The reaction is advantageously carried out in a suitable solvent or in a mixture of solvents such as methanol, ethanol, tetrahydrofuran, dimethylformamide, conveniently at temperatures of between 0–50° C., preferably at temperatures of between 0–30° C. Sodium cyanoborohydride is the reducing agent of choice as it selectively reduces imines while it doesnot reduce oxo-group (so that the yet unreacted starting (6) is basically not reduced to an alcohol in a side reaction), although other conventional metal hydrides as sodium borohydride or diisobutylaluminium hydride can also be employed. Alternatively, the reaction may be performed under conditions of catalytic hydrogenation; however, care is to be taken in selection of hydrogenation catalysts as the sulphur present in the molecule of the substrate can poison the catalyst. Useful hydrogenation catalyst is e.g. palladium/carbon catalyst.

When using an alkylamine for reductive amination, an imine of the formula (10)

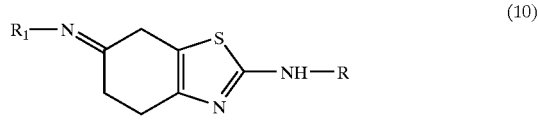

(10)

wherein R and $R_1$ are the same as above, is formed as an intermediate. Such compound may be isolated in case of need and can be subjected to a reduction to (1) in a separate step.

If using conventional reduction or hydrogenation agents, the desired compound (1) is formed as a racemate; however, in a specific feature of the invention, there may be employed also agents allowing enantioselective reductive amination, thus yielding a compound of formula (1) which is enriched by the desired enantiomer. Such agents are known in the art, e.g. as described in U.S. Pat. No. 5,292,893 or WO 97/11934.

The reductive amination of a compound (6), particularly an enantioselective reductive amination, may be also performed indirectly. This alternative is useful for preparation of compounds of formula (1) wherein the substituent $R_1$ is an alkyl group of at least three carbon atoms. The reaction partner of the compound of the formula (6) is now a precursor of the amine (7)—a chiral amine of the formula (7a)

(7a)

bearing a hydrogen-replaceable substituent X on the centre of chirality. Such an amine reacts with the compound (6)—under conditions substantially identical with those as described above- to yield a compound of the formula (11).

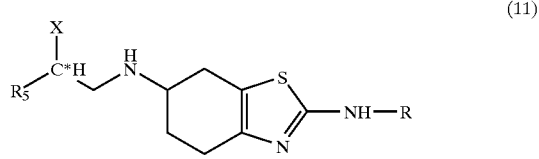

(11)

The presence of a centre of chirality in (7a) aids to direct the reductive amination asymetrically so that the compound (11) may be preparable as enriched by one enantiomer.

In a subsequent step, the substituent X should be replaced by hydrogen to form the compound of formula (1), substantially without racemization on the tetrahydrobenzthiazole ring. Any substituent replaceable by hydrogen but resistant to the conditions of reductive amination may be chosen; advantageously, the starting chiral amine (7a) may be an amine wherein X is a hydroxy group or a halogen atom.

It is apparent that the substituent $R_5$ in the compounds (7a) and (11) is a precursor for the $R_1$ substituent and should be an alkyl group of two carbon less than the desired group $R_1$. Furthermore it is apparent that $R_5$ and X must not be identical to maintain the chiral centre.

The compounds of general formula (11), the process of their formation and that of their transformation to compounds (1) are novel and form another aspect of the present invention.

Another alternative of reductive amination is based on the reaction of a compound of formula (6) with N-alkylhydroxylamine. In this case, an iminoxide is formed as the intermediate and it may be reduced similarly as the imine. Reduction of the iminoxide may also produce a compound enriched by one enantiomer.

The enrichment, in optimum case, could be close to 100%. If not, the amount of undesired enantiomer in the product may be further diminished by means of conventional optical resolution, e.g. by fractional crystallisation of salts with an optically active acid or by chromatography on a chiral phase.

Before or after the reductive amination, the acyl group R may be hydrolysed to hydrogen, if desired. Such hydrolysis can be performed by conventional methods, preferably by alkaline hydrolysis.

If the product of the reductive amination (with or without a subsequent resolution into optical enantiomers) is a compound wherein $R_1$ is hydrogen, it may be converted into another compound of formula (1) wherein $R_1$ is an alkyl group or an aralkyl group, by conventional methods of alkylation or aralkylation of primary amines.

The compounds of formula (1) may be isolated from reaction mixture as free bases or they may be converted into acid addition salts and isolated in solid state by methods known per se. Preferred acids useful to form addition salts are pharmaceutically acceptable acids such as, e.g. hydrochloric, hydrobromic, sulfuric, phosphoric, acetic, oxalic, maleic, fumaric, tartaric, malic, benzoic, methanesulfonic, benzenesulphonic or p-toluenesulfonic acid. The compounds or salts thereof may be also isolated in solvated or hydrated form.

Specifically, the process of our invention and the novel intermediates resulted therefrom are advantageous in the preparation of pramipexole. In the most preferred arrangement for production of praripexole, the bromination reaction of 1,4-cyclohexandione is carried out in methanol under temperatures close to ambient, and the reaction with thiourea with the product of brormination is performed without isolation thereof, i.e. in the same reaction vessel. The product of the condensation, either the ketal or the ketone, is insoluble in the reaction medium and can be easily isolated by conventional methods of filtration or centrifugation, as a hydrobromide or as a free base. If necessary, this intermediate product may be further purified by conventional methods, e.g. by crystallisation.

In the following step, the above intermediate reacts with propylamine and/or with a salt of propylamine, in a presence of a reducing agent such as sodium cyanoborohydride, in temperatures close to ambient and in an inert organic solvent. The intermediating imine is not isolated. After removal of inorganic salts and the excess of propylamine, the desired product can be isolated as a salt with an inorganic or organic acid, e.g. with hydrochloric acid, by crystallisation from a suitable solvent, e.g. from ethanol.

Alternately, undirect reductive amination with a chiral amine as described above may be employed for the pramipexole synthesis. The advantageous chiral amine for this reaction is S(-) 2-hydroxypropylamine. The intermediating product is 2'-hydroxypramipexole (compound (11), $R_5$=$CH_3$, X=OH) and, in the subsequent step, the OH— group on the side chain thereof is removed by a suitable dehydroxylation agent or method, e.g via a iodo-compound (compound (11), $R_5$=$CH_3$, X=J).

If the produced pramipexole is a racemate or it is not sufficiently enriched by the desired S(-) enantiomer, there may be employed a step of optical resolution, i.e. the removal of the undesired R(+) enantiomer by a fractional crystallisation of salts of both enantiomers of pramipexole with an optically active acid. Advantageously, L(+) tartaric acid is suitable for use in such resolution step.

The present invention is more particularly described and explained by the following examples. It is to be understood, however, that the present invention is not limited to these examples and various changes and modifications may be made without departing from the scope of the present invention.

EXAMPLES

Example 1

Preparation of 2-amino-6-oxo-4,5,6,7-tetrahydrobenzothiazole [Compound (6), R=H, $R_3$+$R_4$=oxo]

8.8 g of 1,4-cyclohexanedione was dissolved with 40 mL of methanol. Solution was cooled to 10C and 4.2 mL of bromine was dropwise added at this temperature during 15 minutes. The temperature was kept at 10C for one hour and then allowed to rise to 20C. When bromine colour faded, 7.2 g of thiourea was added. The reaction mixture was then diluted with 20 mL of water and heated under reflux for 2 h. White precipitate was removed by filtration and filtrate was concentrated in vacuo and cooled. The crystals of product (6) were filtered off and washed with a cold water.

$^1$H-NMR spectrum in $D_2O$: 2.12 ppm (t, 2H) C(4); 2.59 ppm (t, 2H) C(5); 2.86 ppm (s, 2H) C(7); 4.76 ppm (solvent)

Example 2

Preparation of 2-amino-6,6-dimethoxy-4,5,6,7-tetrahydrobenzothiazole hydrobromide [Compound (6), R=H, R=methoxy, R=methoxy]

30 g of 1,4-cyclohexanedione was dissolved in 140 mL of methanol. Solution was cooled to 10° C. and 13.6 mL of bromine was dropwise added at this temperature during 15 minutes. The temperature was kept at 10° C. for one hour and then allowed to rise to 20° C. When bromine colour faded, 24.5 g of thiourea was added. The reaction mixture was then stirred overnight at ambient temperature. After cooling down to 5° C., the precipitated crystals of the product were filtered off and washed with cold methanol. Yield: 54.8 g. For analytical purposes, a sample of the product was recrystalized from hot methanol.

$^1$H-NMR spectrum in $D_2O$: 2.05 ppm (t, 2H C(4); 2.50 ppm (t, 2H) C(5); 2.79 ppm (s, 2H) C(7); 3.24 ppm (s, 6H) $CH_3$.

$^{13}$C-NMR in DMSO: C(4) 21.98 ppm, C(5) 28.02 ppm, C(7) 32.41 ppm, C(6) 100.8 ppm; thiazole ring C(2') 164 ppm, C(4') 134 ppm, C(5') 112 ppm; methoxy group 48.3 ppm.

Example 3

Preparation of 2-amino-6-oxo-4,5,6,7-tetrahydrobenzothiazole [Compound (6), R=H, $R_3$+$R_4$=oxo]

21.9 g of the dimethoxy compound from example 2 was suspended in 205 ml of water and heated to 45° C. for dissolution. Then 7.3 ml of concentrated HCl was added and the solution was stirred at 60° C. for 30 minutes. Reaction mixture was cooled to ambient temperature and neutralised with 40% aqueous NaOH. Precipitated solid was filtered off, washed with water and dried to yield 10.9 g of the title product. For analytical purposes, the sample of the product was recrystalized from hot isopropanol.

$^1$H-NMR in DMSO: 2.78 ppm (t, 2H) C(4); 2.61 ppm (t, 2H) C(5); 3.37 ppm (s, 2H) C(7)

$^{13}$C-NMR in DMSO: C(4) 25.09 ppm, C(5) 38.87 ppm, C(7) 37.08 ppm, C(6) 207.07 ppm; thiazole ring C(2') 167.1 ppm; C(4') 144.08 ppm, C(5') 111.00 ppm

Example 4

Preparation of (±)2-amino-6-propylamino-4,5,6,7-tetrahydrobenzothiazole [Compound (1), R=hydrogen, $R_1$=propyl, $R_2$=hydrogen]

3.0 g of propylamine hydrochloride was dissolved in 60 mL of methanol and 2.2 g of 2-amino-oxo-4,5,6,7-tetrahydrobenzothiazole was added. 1.1 mL of propylamine was poured into the mixture to set pH within the range 6.5–7.0. Then 0.7 g of sodium cyanoborohydride was added and the reaction mixture was stirred for 70 hours under nitrogen atmosphere and at ambient temperature. The reaction mixture was diluted with 50 mL of water and 10 mL of conc. hydrochloric acid. Solvents were removed by evaporation, the yellow residue was stirred with ethanol and the solid was removed by filtration. The filtrate was made alkaline with potassium hydroxide solution and the precipitate was again removed by filtration. Filtrate was several times evaporated with ethanol to remove propylamine. The residue was dissolved in hot ethanol and resulting crystals were collected and dried. Reaction product was characterised by NMR spectra.

1H-NMR spectrum in CDCl3: 0.93 ppm (t, 3H) C(3'); 1.51 ppm (sextet, 2H) C(2'); 2.65 (t, 2H) ppm (s) C(1'); 2.6 ppm (m, 2H) C(4); 1.9 ppm (1H)+1.70 ppm (m, 1H) C(5); 2.98 ppm (m, 1H) C(6); 2.82 ppm (dd, 1H)+2.40 ppm (m, 1H) C(7);

13C-NMR in CDCl3: C(4) 29.47 ppm, C(5) 24.92 ppm, C(7) 30.1 ppm, C(6) 53.92 ppm, C(1') 49.20 ppm, C(2') 23.48 ppm, C(3') 11.76 ppm; thiazole ring C(2') 165.49 ppm; C(4') 145.02 ppm, C(5') 116.31 ppm

Example 5

Preparation of 2-acetamido-6-oxo-4,5,6,7-tetrahydrobenzothiazole hydrobromide [Compound (6), R=acetyl, $R_3$+$R_4$=oxo]

8.8 g of 1,4-cyclohexanedione was dissolved in 40 ml of methanol. The solution was cooled on an ice bath to 10° C. and 4.4 ml of bromine was added dropwise in 10 minutes. The solution was stirred at the same temperature for 1.5 hours and then the temperature was allowed to rise to ambient. After the colour disappeared, 11.1 g of N-acetylthiourea and 20 ml of water were added and the solution was heated under reflux for 2 hours. Hot reaction mixture was filtered, the filtration cake was washed with hot methanol and the combined filtrates were heated to reflux with activated charcoal. The hot suspension was filtered and the filtrate was concentrated in vacuo to yield 3.4 g of a solid product.

Example 6

Preparation of Pramipexole Dihydrochloride from (±)2-amino-6-propylamino-4,5,6,7-tetrahydrobenzothiazole 5 g of (±)2-amino-6-propylamino-4,5,6,7-tetrahydrobenzothiazole was dissolved in 25 ml of methanol and 4.0 g of L(+)-tartaric acid was added under stirring. The mixture was cooled and the white crystals were filtered off, washed with methanol and dried to yield 4.8 g of pramipexole tartrate. The crystals were dissolved in 10 ml of water and concentrated hydrochloric acid was added to dissolve the solid. The solution was cooled to 10° C. and a solution of 10 g of potassium hydroxide in 10 ml of water was added. The mixture was stirred for 30 minutes and the white crystals were removed by filtration and washed with cold water. The crystals were redissolved in 7 ml of ethanol and gaseous hydrogen chloride was bubbled through the solution at 10° C. After 1 hour of stirring, the precipitated solid was separated by filtration, washed with cold ethanol and dried to yield 2.1 g of white crystals. The product is identical with pramipexole dihydrochloride by NMR and has optical rotation [α](20,D)=−48,78° (c=1, MEOH)

Example 7

Preparation of 2,6-diamino-4,5,6,7-tetrahydro-1,3-benzothiazole [Compound (1), R=$R_1$=$R_2$=hydrozen]

A solution of 2-amino-6-oxo-4,5,6,7-tetrahydro-1,3-benzothiazole (2.0 g, 12 mmol), ammonium acetate (9.2 g, 120 mmol) and sodium cyanoborohydride (0.53 g, 8.4 mmol) in 40 mL of methanol was stirred under nitrogen at ambient temperature for 48 hours. Concentrated HCl was added and methanol was removed in vacuo. The residue was mixed with water and solution was made alkaline with NaOH. White precipitate was removed by filtration, washed with water and dried to give 1.0 g of the title compound. The structure of the product was confirmed by NMR.

Example 8

Preparation of 2-amino-6-propylamino-4,5,6,7-tetrahydrobenzothiazole using S(+) 1-amino-2-propanol Step 1) Preparation of (2)S-1-(2'-amino-4',5',6',7'-tetrahydro-benzothiazol-6'-ylamino)-propan-2-ol [Compound (1), R=H, $R_1$=2(S)-hydroxypropyl, R2=hydrogen]

6.7 g of S-(+)-1-amino 2-propanol was dissolved in 125 mL of methanol and 10 g of 2-amino-6-oxo-5,6,7,8-tetrahydrobenzthiazole was added under nitrogen. The yellow suspension was stirred at 5–7 C for 20 minutes and 3,85 g of sodium cyanoborohydride was added. After 20 hours of stirring the reaction mixture was acidified with hydrochloric acid and the solvent was removed in vacuo. Crystalline residue was dissolved in water and water solution was alkalised with 25% aqueous NaOH. Precipitated solid was filtered off, washed with cold water and dried to yield 5.5 g of the title product (m.p. 75–85° C.).

$^1$H-NMR in DMSO: 1.14 ppm (d, 3H) C(3'); 4.12 ppm (m, 1H) C(2'); C(1') 3.0 ppm (m, 2H); 3.54 ppm (m, 1H) C(6); 3.10 ppm (m, 2H) C(7); 2.34 ppm (2H) C(3); 2.09 ppm (m, 2H) C(4)

$^{13}$C-NMR in DMSO: C(4) 23.2 ppm, C(5) 20.9 ppm, C(7) 24.69 ppm, C(6) 52.65 ppm, C(1') 51.51, C(2') 62.30, C(3') 21.02 ppm; thiazole ring C(2') 168.7 ppm; C(4') 132.8 ppm, C(5') 110.83 ppm Step 2: Preparation of (2'S)-N-6-(2'-Iodo-propyl)-4,5,6,7-tetrahydro-benzothiazole-2,6-diamine dihydroiodide [Compound (1), R=H, R1=2(S)-iodopropyl, R2=hydrogen]

5.0 g of the product of Step 1, 5.0 g of red phosphorus and 150 mL of 57% hydroiodic acid was refluxed for 25 hours. Reaction mixture was filtered and the filtrate was evaporated in vacuo. The crystalline residue was stirred with acetone, crystals removed by suction and washed with acetone to give 6.5 g of the title product with m.p. 213–222C.

$^1$H-NMR in DMSO: 2.0 ppm (d, 3H) C(3'); 4.45 ppm (m, 1H) C(2'); 3.62 ppm (m, 2H) C(1'); 2.80 ppm (m, 1H) C(4); 2.1–2.5 ppm (m, 2H) C(5); 3.87 ppm (m, 2H) C(6); 3.2 ppm (m, 2H) C(7)

$^{13}$C-NMR in DMSO: C(4) 17.42 ppm, C(5) 17.17 ppm, C(7) 26.09 ppm, C(6) 56. ppm, C(1') 55.54, C(2') 26.90 ppm, C(3') 22.42 ppm; thiazole ring C(2') 171.0 ppm, C(4') 134.34 ppm, C(5') 112.88 ppm Step 3: Preparation of 2-amino-6-propylamino-4,5,6,7-tetrahydrobenzothiazole 6.0 g of the product of Step 2 was dissolved in 100 mL of water acidified with 1 mL of 36% hydrochloric acid. 0.3 g of 10% Pd/C catalyst was added and the reaction mixture was hydrogenated at 100° C. and 4.0 MPa of hydrogen for 8 hours. Catalyst was filtered off, washed with water and the filtrate was made alkaline with addition of 50% sodium hydroxide solution. Precipitated product was filtered off, washed with water and air-dried to give 1.8 g of the title product with m.p. 145–150° C. and optical purity 42%.

Example 9

Preparation of (±) 2-amino-6-propylamino-4,5,6,7-tetrahydrobenzothiazole [Compound (1), R= hydrogen, $R_1$=propyl, $R_2$=hydrogen] Dihydrochloride A 150 mL Paar autoclave was charged with 3.5 g of 2-amino-6-oxo-4,5,6,7-tetrahydrobenzthiazole, 50 mL of tetrahydrofuran, 2.0 mL of propylamine and 0.8 g of 10% Pd/C catalyst. The reaction mixture was heated at 100° C., 40 bars of hydrogen and 400 RPM for 48 h. Catalyst was removed by filtration, filtrate evaporated to dryness, the residue dissolved in ethanol and solution saturated with gaseous hydrogen chloride. Precipitated crystals were removed by suction, washed with ethanol and dried to give crystalline product with m.p. 268–278° C.

Example 10

Preparation of (+) 2-amino-6-oxo-4,5,6,7-tetrahydrobenzothiazole [Compound (6), R=H, $R_3$+ $R_4$=oxo]hydrobromide 340 g of 2-amino-6,6-dimethoxy-4,5,6,7-tetrahydrobenzothiazole hydrobromide (Example 2) was mixed with 290 mL of hot water. The mixture was evaporated under reduced pressure at low temperature (50–55° C.), and the residue was three times evaporated with 170 mL of acetone. The residue was mixed with 340 mL of acetone and after 1 hour of stirring the solid was filtered off and air dried to give 168 g of the title product.

Example 11

Preparation of (+)2-amino-6-propylamino-4,5,6,7-tetrahydro benzothiazole 10 g of 2-amino-6-oxo-4,5,6,7-tetrahydrobenzthiazole hydrobromide was added to the mixture of 5 mL of propylamine and 125 mL of methanol under nitrogen. The mixture was stirred for 20 minutes. Then 2,7 g of sodium cyanoborohydride was added in parts during 30 minutes. The solution was acidified with 2 mL of acetic acid to the value pH=7–8. Reaction mixture was worked up after 20 hours of stirring by addition of 8 mL of HCl. Precipitated solid was removed by suction and the filtrate was evaporated to dryness. The solid residue was heated at reflux with 250 mL of ethanol for 20 minutes. Undissolved part was filtered off and the hot filtrate was concentrated under reduced pressure and cooled on an ice bath. Precipitated crystals were removed by suction and the cake was washed with cold ethanol to give 5.1 g of a product with m.p. 245–257° C.

The solid product was dissolved in 28 mL of of water and the solution was alkalinized with 25% aqueous NaOH. The mixture was stirred for 2 hours and precipitated crystals were removed by suction and washed with water to give 2.7 g of the title product with m.p. 147–149° C.

What is claimed is:

1. A process which comprises bromination of 1,4-cyclohexanedione by bromine in an alcoholic solvent, followed by treatment of the reaction mixture with thiourea or N-acylthiourea and isolation of a compound of formula (6)

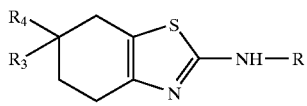

(6)

wherein R is hydrogen or acyl group, $R_3$ and $R_4$ are either the same and each of them represents an alkoxy group of 1–4 carbons or they together form an $C_2$–$C_5$ alkylenedioxy group or an oxo-group, or an acid addition salt thereof, from the reaction mixture.

2. A process according to claim 1 wherein the alcoholic solvent is selected from the group consisting of methanol, ethanol, n-propanol, ethylene glycol and 2,2-dimethylpropyleneglycol.

3. A process according to claim 2 wherein the solvent is methanol.

4. A process according to claim 1 wherein the reaction mixture is treated with thiourea.

5. A process according to claim 1 which further comprises preparing a compound of formula (1)

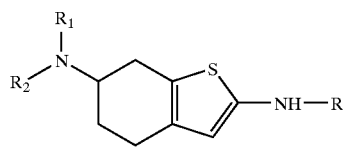

(1)

wherein R is hydrogen or acyl group, $R_1$ is hydrogen, lower alkyl or aralkyl group and $R_2$ is hydrogen, which comprises reacting said compound of formula (6) with either (A) an amine of the formula (7)

$R_1$-$NH_2$ (7)

wherein $R_1$ is as hereinbefore defined, under presence of a reduction agent or a hydrogen gas with hydrogenation catalyst or, alternatively, isolating the mime intermediate and reducing it by reaction with said reduction agent or by hydrogenation, to form said compound of formula (1) or, (B) reacting said compound of formula (6) with a chiral amine of formula (7a)

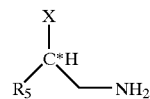

(7a)

wherein $R_5$ is an alkyl group of two carbons less than $R_1$, and X is a hydrogen-replaceable leaving group not identical with $R_5$, under presence of a reduction agent or a hydrogen gas with hydrogenation catalyst or, alternatively, isolating the imine intermediate and reducing it by reaction with said reduction agent or by hydrogenation, to yield a compound of formula (11)

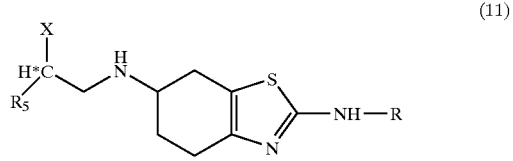

(11)

followed by a step of substitution of the group X in the compound of formula (11) for hydrogen to form said compound of formula (1).

6. A process according to claim 5 wherein the reduction agent is a metal hydride.

7. A process according to claim 5 wherein the reduction agent is an agent allowing forming a product enriched with one enantiomer thereof.

8. A process according to claim 5 further comprising a step of hydrolysis of the acyl group to hydrogen, when a compound of formula (1) with R=acyl is produced by said process.

9. A process according to claim 5 wherein in the chiral amine of formula (7a) R is hydrogen, $R_5$ is methyl and X is hydroxy or halogen group.

10. A process according to claim 5 wherein the obtained compound of formula (1) is a mixture of optical isomers enriched with one of the optical isomers.

11. A process according to claim 5 further comprising a step of resolving the obtained compound of formula (1) into single optical enantiomers thereof.

12. A process according to claim 5 further comprising a step of isolation of the resulted compound of formula (1) from the reaction mixture as a free base or as an acid addition salt.

13. A process according to claim 12 wherein the isolated product is substantially S(-)2-amino-6-propylamino-4,5,6,7-tetrahydrobenzothiazole (pramipexole) or its acid addition salts.

14. A process according to claim 13 wherein the product is isolated as the dihydrochloride.

15. A process according to claim 5 which comprises reacting a propylamine and/or its salt with a compound of formula (6) selected from the group consisting of 2-amino-6-oxo-4,5,6,7-tetrahydrobenzothiazole, 2-amino-6,6-dialkoxy-4,5,6,7-tetrahydrobenzothiazole and a mixture of both compounds, under presence of a reduction agent or a hydrogen gas with hydrogenation catalyst or, alternatively, isolating the imine intermediate and reducing it by reaction with said reduction agent or by hydrogenation, to form 2-amino-6-propylamino-4,5,6,7-tetrahydrobenzothiazole as said compound of formula (1).

16. A process according to claim 15 further comprising the step of resolving 2-amino-6-propylamino-4,5,6,7-tetrahydrobenzothiazole into its enantiomers using L(+) tartaric acid as the resolution agent and isolating the enantiomer.

17. The process according to claim 16 wherein the isolated product is substantially S(−)2-amino-6-propylamino-4,5,6,7-tetrahydrobenzothiazole (pramipexole) or its acid addition salt.

18. A process according to claim 1 wherein R is hydrogen or acetyl group and $R_3$ and $R_4$ each represent methoxy, ethoxy or n-propoxy group.

19. A process according to claim 1 wherein $R_3$ and $R_4$ together form an oxo group.

20. A process according to claim 1 wherein said compound of formula (6) is selected from the group consisting of 2-amino-6-oxo-4,5,6,7-tetrahydrobenzthiazole, 2-amino-6,6-dimethoxy-4,5,6,7-tetrhydrobenzothiazole, 2-acetamido-6-oxo-4,5,6,7 tetrahydrobenzothiazole, 2-acetamido-6,6-dimethoxy-4,5,6,7-tetrahydrobenzthiazole, and acid addition salts thereof.

21. A process which comprises brominating in an alcoholic solvent 1,4-cyclohexanedione with bromine followed by treating the reaction product with thiourea or N-acylthiourea to form a compound of formula (6)

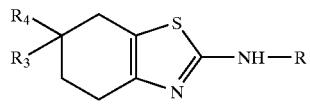

(6)

wherein R is hydrogen or acyl group, $R_3$ and $R_4$ are either the same and each of them represents an alkoxy group of 1–4 carbons or they together form an $C_2$–$C_5$ alkylenedioxy group or an oxo-group, or an acid addition salt thereof; and converting said compound of formula (6) to a compound of formula (1)

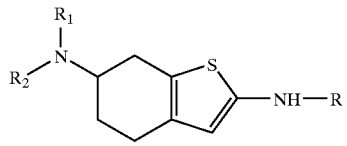

(1)

wherein R is hydrogen or acyl group, $R_1$ is hydrogen, lower alkyl or aralkyl group and $R_2$ is hydrogen, by reductive amination with ammonia or alkylamine of formula (7)

$R_1$–$NH_2$ wherein $R_1$ is as defined above, and a reducing agent.

22. A process according to claim 21 wherein said alcoholic solvent is methanol, and said alkylamine is propylamine.

23. The process according to claim 22 wherein said compound of formula (1) produced by said process is pramipexole.

* * * * *